United States Patent
Robichaud et al.

(10) Patent No.: US 6,599,756 B1
(45) Date of Patent: *Jul. 29, 2003

(54) DETECTION OF ANTIBODIES TO GLYCOSPHINGOLIPIDS USING SOLID-PHASE REACTANTS COATED WITH CARBONYL GROUPS

(75) Inventors: Normand J. Robichaud, Leominster, MA (US); Louis P. Kertiles, Petersham, MA (US)

(73) Assignee: Athena Diagnostics, Inc., Worcester, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/626,685

(22) Filed: Jul. 27, 2000

(51) Int. Cl.[7] .................. G01N 33/53; G01N 33/543
(52) U.S. Cl. .................. 436/518; 435/7.1; 435/7.72; 435/7.9; 435/7.92; 435/39; 435/967; 435/975; 436/501; 436/507; 436/513; 436/524; 436/536; 436/538; 436/540; 436/542; 436/543; 436/546; 436/811
(58) Field of Search ................. 435/7.1, 7.72, 435/7.9, 7.92, 39, 967, 975; 436/501, 513, 507, 518, 524, 536, 538, 540, 542, 543, 546, 811

(56) References Cited

U.S. PATENT DOCUMENTS

| | | | |
|---|---|---|---|
| 6,077,681 A | | 6/2000 | Pestronk .................. 435/7.92 |
| 6,352,831 B1 | * | 3/2002 | Buschard et al. ............ 435/7.1 |
| 6,448,023 B1 | * | 9/2002 | Skinner et al. ................ 435/8 |

FOREIGN PATENT DOCUMENTS

WO    WO 98/35233 A1  *  8/1998

OTHER PUBLICATIONS

Voet et al. Biochemistry, p. 277 (1990).*
Van den Berg, L., et al., "Anti–MAG and Anti–SGPG Antibodies in Neuropathy," *Muscle Nerve*, 19(5):637–643 (1996).

Miyatani, N., et al., "Glycosphingolipids in the Cerebrospinal Fluid of Patients with Multiple Sclerosis," *Mol. Chem. Neuropathol.*, 13(3):205–216 (1990).

Ilyas, A.A., et al., "Antibodies to Sulfated Glycolipids in Guillain–Barre Syndrome," *J. Neurol. Sci.*, 105(1):108–117 (1991).

Yuki, N., et al., "Correlation Between Cytomegalovirus Infection and IgM Anti–MAG/SGPG Antibody Associated Neuropathy," *Ann. Neurol.*, 44(3):408–410 (1998).

Yuki, N., et al., "Autoantibodies to Peripheral Nerve Glycosphingolipids SPG, SLPG, and SGPG in Guillain–Barre Syndrome and Chronic Inflammatory Demyelinating Polyneuropathy," *J. Neuroimmunol.*, 70(1):1–6 (1996).

Hauttecoeur, B., et al., "Reactivity of Human Monoclonal IgM with Nerve Glycosphingolipids," *Clin. Exp. Immunol.*, 80(2):181–185 (1990).

Younes–Chennoufi, B.A., et al., "Anti–sulfoglucuronyl Paragloboside IgM Antibodies in Amyotrophic Lateral Sclerosis," *J. Neuroimmunol.*, 57(1–2):111–115 (1995).

Lauritzen, E., et al., "Peptide dot immunoassay and immunoblotting: Electroblotting from aluminum thin–layer chromatography plates and isoelectric focusing gels to activated nitrocellulose".

* cited by examiner

*Primary Examiner*—Long V. Le
*Assistant Examiner*—Kartic Padmanabhan
(74) *Attorney, Agent, or Firm*—Hamilton, Brook, Smith & Reynolds, P.C.

(57) ABSTRACT

Methods of detecting antibodies to one or more glycosphingolipid(s) of interest in a sample are disclosed which comprise using a solid-phase reactant having carbonyl groups attached thereon, and the glycosphingolipid(s) of interest linked to the solid-phase reactant by an amide bond between an amino group of the glycosphingolipid of interest and a carbonyl group attached to the solid-phase reactant. The methods of detecting antibodies to glycosphingolipid(s) of interest can be used in methods of diagnosing autoimmune diseases in an individual.

10 Claims, 1 Drawing Sheet

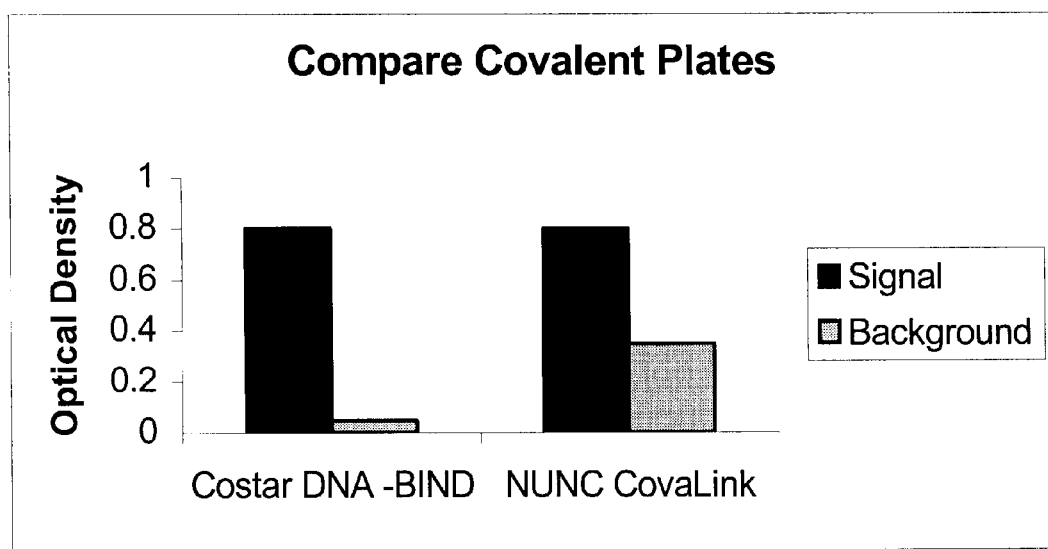

DETECTION OF ANTIBODIES TO GLYCOSPHINGOLIPIDS USING SOLID-PHASE REACTANTS COATED WITH CARBONYL GROUPS

BACKGROUND OF THE INVENTION

Antibodies to the glycosphingolipid, sulfoglucuronyl paragloboside (SGPG) have been implicated in many different autoimmune diseases. For example, serum IgM antibodies to GM ganglioside have been found in patients with amyotrophic lateral sclerosis (ALS) (Younes-Chennoufi, B. A. et al., *J. Neuroimmunol.* 57:111–5 (1995)) chronic inflammatory demyelinating polyneuropathy (Yuki, N. et al., *J. Neuroimmunol.* 70:1–6 (1996)), and acute Guillain-Barre syndrome (Ilyas, AA. et al., *J. Neurol. Sci.* 105:108–17 (1991)).

Enzyme-linked immunosorbent assays (ELISA) have been used for identification of anti-glycosphingolipid antibodies; however, high background values frequently interfere with accurate assessment of the amount of such antibodies. Reliable measurement of anti-glycosphingolipid antibodies is critical for correct diagnosis of immune diseases.

SUMMARY OF THE INVENTION

The present invention pertains to methods of determining, in a test sample, the amount of antibodies directed against a specific nervous system antigen or antigens, using a modified solid-phase reactant. The method utilizes a solid-phase reactant, such as a microtiter plate, that is modified with carbonyl groups attached to its surface. One or more glycosphingolipids of interest (e.g., sulfoglucuronyl paragloboside (SGPG))are linked to the modified solid-phase reactant by an amide bond between an amino group of the glycosphingolipid and a carbonyl group attached to the solid-phase reactant. One or more control antigens, such as other glycosphingolipids, glycolipids, glycoproteins, gangliosides or carbohydrates, can also be attached on the surface of the modified solid-phase reactant. The modified solid-phase reactant having gycosphingolipid(s) of interest linked thereon is contacted with a test sample, such as a test sample of a bodily fluid (e.g., blood, serum, cerebrospinal fluid, or urine) from an individual, under conditions such that any antibody to the gycophingolipid(s) of interest that may be present in the test sample can bind to the glycosphingolipid(s) of interest linked to the modified solid-phase reactant. The amount of antibodies in the test sample to the glycosphingolipid(s) of interest is then determined using standard methods, such as enzyme-linked immunosorbent assay (ELISA) or another appropriate solid-phase assay. If a control antigen is attached on the modified solid-phase reactant, the level of antibodies in the test sample to the control antigen, can also be determined using the same methods. Specific reactivity of antibodies to the glycosphingolipid of interest is determined by the amount of antibody binding to the glycosphingolipid of interest that is above the amount of antibody binding to the control antigen.

The methods can be used in diagnosis of autoimmune diseases in an individual. The amount of antibody to a glycosphingolipid of interest in a test sample from the individual is determined using the methods. An amount of antibody to a glycosphingolipid of interest that is greater, by an amount that is statistically significant, than the amount of antibody to the glycosphingolipid of interest in a control sample, may be indicative of the presence of an autoimmune disease. Alternatively, an amount of antibody to a glycosphingolipid of interest that is equal to or greater than an established reference amount may be indicative of the presence of the disease. For example, the methods can be used as a preliminary screening assay; an amount of antibody to a glycosphingolipid of interest that is greater, by an amount that is statistically significant, than the amount of antibody to the glycosphingolipid of interest in a control sample, or an amount of antibody to a glycosphingolipid of interest that is equal to or greater than an established reference amount, is considered a "positive" screening result that substantiates additional study of other antibodies that are involved in autoimmune disease.

The invention also pertains to test kits, containing modified solid-phase reactants, for use in the methods of the invention.

The high sensitivity and specificity of the methods can clarify the differential diagnosis of autoimmune diseases. Furthermore, a modified solid-phase reactant having carbonyl groups attached to its surface allows the use of a smaller amount of glycosphingolipid than the amount which would otherwise be necessary to perform similar assays with a solid-phase reactant not having this modification. In addition, a modified solid-phase reactant having carbonyl groups attached to its surface can be coated with a glycosphingolipid of interest without a need for toxic solvents; the coating is not affected by humidity, and yields consistent and reproducible assay results.

BRIEF DESCRIPTION OF THE DRAWING

The FIGURE is a graphic depiction of a comparison of signal to background noise of two types of solid phase reactants. Black, signal; grey, background.

DETAILED DESCRIPTION OF THE INVENTION

A description of preferred embodiments of the invention follows.

The invention described herein relates to methods of determining the amount of antibodies to one or more glycosphingolipid(s) of interest in a sample. The invention further pertains to methods of diagnosing autoimmune diseases in an individual by determining the amount of antibodies to one or more glycosphingolipid(s) of interest in a sample from the individual. Applicant has discovered that significantly increased sensitivity for antibodies to certain glycosphingolipids can be achieved by conducting an enzyme-linked immunosorbent assay (ELISA) using microtiter plates that are modified with carbonyl groups, allowing amide linkage of glycosphingolipids to the plates.

As a result of this discovery, highly sensitive and specific methods of determining the presence or absence, and the amount, of antibody to one or more glycosphingolipid(s) of interest in a sample are now available. In the methods, a modified solid-phase reactant is used. The term, "solid-phase reactant", as used herein, refers to a solid medium, such as a microtiter plate, a membrane (e.g., nitrocellulose), a bead, a dipstick, a thin-layer chromatographic plate, or other solid medium. In a preferred embodiment, the solid-phase reactant is a microtiter plate that can be used in a solid-phase immunoassay, such as an enzyme-linked immunosorbent assay. The solid-phase reactant is modified such that carbonyl groups are grafted into the reactant. As a result of the presence of the carbonyl groups, certain antigens, such as glycosphingolipids, can be linked on the surface of the solid-phase reactant by an amide bond between the carbonyl group on the solid-phase reactant and the amino group of the antigen. A representative solid-phase reactant that allows linkage of antigens on its surface in this manner is the Co-star DNA-BIND covalent plate (Co-star, Corning, N.Y.). A solid-phase reactant that has carbonyl groups attached thereon arid therefore has the ability to allow amide bond linkage of antigens onto its surface is referred to herein as a "modified solid-phase reactant".

One or more glycosphingolipid(s) of interest is linked to the modified solid-phase reactant. A glycosphingolipid of interest that is "linked" or "attached" to the modified solid-phase reactant is a glycosphingolipid that has formed an amide bond between an amino group of the glycosphingolipid and the carbonyl group attached to the modified solid-phase reactant. Representative glycosphingolipids include sulfoglucuronyl paragloboside (SGPG). One type of glycosphingolipid can be used; alternatively, more than one type of glycosphingolipid can be linked to the covalent-linkage solid-phase reactant. As used herein, a solid-phase reactant having "at least one" glycosphingolipid of interest linked thereon may have only one type of glycosphingolipid of interest thereon, or may also have more than one type of glycosphingolipid of interest thereon. In a preferred embodiment, SGPG is linked to the modified solid-phase reactant. A representative method of linking uses the glycosphingolipid of interest reconstituted in methanol and diluted into phosphate buffered saline. EDAC (1-ethyl-3-(3-diethylaminopropyl)carbodiimide) can also be included, if desired; for example, in one embodiment, if the glycosphingolipid of interest is SGPG, EDAC is included in the solution containing the glycosphingolipid; the solution containing the glycosphingolipid is then allowed to coat the modified solid-phase reactant. Because the modified solid-phase reactant contains carbonyl groups, amino groups present on the glycosphingolipids form amide bonds with the carbonyl groups when exposed to the carbonyl groups on the modified solid-phase reactant. A modified solid-phase reactant on which one or more glycosphingolipid(s) is attached is referred to herein as a "glycosphingolipid modified solid-phase reactant".

A control antigen, such as another glycosphingolipid, or a glycoprotein or carbohydrate, can also be attached to the modified solid-phase reactant. More than one control antigen can be used. A control antigen can be identified, for example, by evaluation of a number of samples from individuals having known disease states. "Specific binding" is indicated by statistically demonstrated binding of antibody in the sample to the antigen of interest, relative to the clinical status (disease state) of the samples (e.g., binding, in a statistically significant number of samples from individuals having a particular disease state, of antibody to the particular antigen). A lack of binding to a particular antigen by a sample from an individual having a known clinical status is generally accepted as being indicative of a non-reactive (control) antigen.

The control antigen(s) can be attached to the modified solid-phase reactant using methods similar to those used to coat the glycosphingolipid(s) of interest onto the modified solid-phase reactant. The control antigen is usually attached to the modified solid-phase reactant at a different location than the glycosphingolipid(s) of interest. For example, if the solid-phase reactant is a microtiter plate, a glycosphingolipid of interest can be attached to certain wells of the plate, and the control antigen can be attached to other wells of the plate. In another example, if more than one glycosphingolipid of interest is attached to the plate, the control antigen is attached to certain wells of the plate; a first glycosphingolipid of interest is attached to other wells of the plate; a second glycosphingolipid of interest is attached to different wells of the plate from either the control antigen or the first glycosphingolipid of interest, etc. Alternatively, the control antigen can be attached to a separate solid-phase reactant, the separate solid-phase reactant being the same type of solid-phase reactant as that onto which the glycosphingolipid(s) of interest is coated. It is intended that the term, "glycosphingolipid modified solid-phase reactant", refers to those modified solid-phase reactants having one or more glycosphingolipid(s) of interest attached thereon, as well as to those modified covalent-linkage solid-phase reactants having one or more glycosphingolipid(s) of interest attached thereon as well as one or more control antigens attached at a different location thereon. The term, "control antigen solid-phase reactant" is used to refer to a solid-phase reactant having solely control antigen(s) attached thereto.

The glycosphingolipid modified solid-phase reactant (and control antigen solid-phase reactant, if used) is used in an assay to determine the amount of antibody to one or more glycosphingolipid(s) of interest in a test sample. The test sample to be assayed for the amount of antibody to a glycosphingolipid of interest can be a sample of bodily fluid or tissue from an individual For example, the test sample can comprise blood, serum, cerebrospinal fluid, urine, nasal secretion, saliva, or any other bodily fluid or tissue. Alternatively, the test sample can comprise antibodies, and particularly IgM, IgG and/or IgA antibodies, that have been isolated from a sample of bodily fluid or tissue from the individual. In a preferred embodiment, the test sample is a serum sample from an individual suspected of having a neuropathy.

To determine the amount of anti-glycosphingolipid antibody in a test sample, the glycosphingolipid modified solid-phase reactant is contacted with the test sample. A glycosphingolipid modified solid-phase reactant that has been contacted with a test sample is referred to herein as a "contacted glycosphingolipid modified solid-phase reactant." The contacted glycosphingolipid modified solid-phase reactant is maintained under appropriate conditions to allow binding of any antibody to the glycosphingolipid(s) of interest that may be present in the test sample, to the glycosphingolipid(s) of interest that is attached to the solid-phase reactant. The term, "antibody to a glycosphingolipid of interest" refers to an antibody or antibodies that preferentially binds to the glycosphingolipid of interest. For example, an antibody to a glycosphingolipid of interest preferentially binds to the glycosphingolipid of interest in an amount that is greater than to control antigens (e.g., glycolipids, glycoproteins or carbohydrates), and/or in an amount that is greater than to other glycosphingolipids, by an amount that is statistically significant.

The amount of antibody to the glycosphingolipid(s) of interest in the test sample, if any, that has bound to the glycosphingolipid(s) of interest on the modified solid-phase reactant is determined. The amount is determined separately for each glycosphingolipid of interest. It is expected that an antibody will specifically interact with a glycosphingolipid of interest; that is, an antibody will interact preferentially with one glycosphingolipid of interest, and not to another glycosphingolipid of interest.

The amount of antibody can be determined by a variety of methods using standard techniques, including enzyme-linked immunosorbent assay (ELISA), solid phase radioimmunoassay, or other solid phase immunoassays (see Ausubel, F. M. et al., eds., Current Protocols in Molecular Biology, John Wiley & Sons, 1996, especially units 11.2

(ELISA) and 11.16 (Determination of Specific Antibody Titer); the entire teachings of this reference are incorporated herein by reference). In a typical solid-phase immunoassay, the amount of antibody bound to the glycosphingolipid of interest attached to the modified solid-phase reactant is determined using a developing reagent, such as a detection antibody that binds to the antibody to the glycosphingolipid of interest. The detection antibody can be linked or conjugated to another molecule, such as an enzyme or fluorophore, to facilitate detection. Alternatively, the detection antibody is iodinated. If more than one glycosphingolipid of interest is used, different detection antibodies can be used to detect each antibody to each glycosphingolipid of interest. For example, a detection antibody that binds to an antibody to one glycosphingolipid of interest can be conjugated to a first fluorophore, and a detection antibody that binds to an antibody to a second glycosphingolipid of interest can be conjugated to a second fluorophore that is distinguishable from the first fluorophore. Alternatively, if the same detection reagent is used, the different glycosphingolipids of interest can be attached to the modified solid-phase reactant at a different, identifiable location, such that the presence of a detection reagent at a particular location corresponds to the presence of antibodies to the glycosphingolipid of interest attached to the modified solid-phase reactant at that location.

In a preferred embodiment, an ELISA assay is performed, using as a developing reagent a detection antibody that is linked to an enzyme, such as horseradish peroxidase. The contacted glycosphingolipid modified solid phase-reactant is incubated with the developing reagent, forming a developed, contacted solid-phase reactant. Subsequently, a substrate of the enzyme is added to the developed, contacted solid-phase reactant, and the amount of activity of the enzyme on its substrate (e.g., the amount of hydrolysis of the substrate) is measured by an appropriate means, such as by measuring optical density.

Titers of antibodies to the glycosphingolipid(s) of interest can be calculated from the amount of detector antibody bound to the antibodies to the glycosphingolipid of interest, using standard conversion algorithms. For example, if the developing reagent comprises horseradish peroxidase, titers of antibody can be calculated as set forth in Pestronk et al. (*Ann. Neurol.* 2.7:316–326 (1990)).

If a control antigen is attached to the modified solid-phase reactant, titers of antibody binding to the control antigen are subtracted from the titers of antibody binding to the glycosphingolipid of interest. The difference between the titer of antibody binding to the glycosphingolipid of interest and the titer of antibody binding to the control antigen(s) is indicative of the specific (selective) binding of the antibody to the glycosphingolipid of interest. If the control antigen is attached to a separate modified solid-phase reactant, the control antigen modified solid-phase reactant is contacted with the test sample in the same manner as the glycosphingolipid modified solid-phase reactant and maintained under the same conditions. The amount of antibody to the control antigen is determined by the same method as is used to determine the amount of antibody to the glycosphingolipid of interest.

Autoimmune diseases, particularly immune-mediated neuropathies, can be diagnosed using these methods of determining the amount of antibody to a glycosphingolipid of interest. To diagnose a disease of interest, the test sample is a sample from an individual to be tested for the presence of a neuropathy. The amount of antibody to a glycosphingolipid(s) of interest in the test sample is compared with the amount of comparable antibody to the glycosphingolipid(s) of interest in at least one comparable control sample (i.e., a sample of the same type(s) of antibody (IgM, IgG, and/or IgA) from an individual who is not afflicted by the disease of interest). The control sample can be a sample from any individual who is not afflicted with the disease of interest; it is not necessary that the control sample be from an individual who is free of disease. For example, the control sample can be a sample from an individual who has a different immune-mediated disease, or systemic immune disorders. A "comparable" normal sample is a sample of the same type of body fluid or tissue as the test sample; alternatively, if the test sample is IgM antibodies isolated from a sample of fluid or tissue, the comparable normal or control sample is a sample of IgM antibodies isolated from the same type of bodily fluid or tissue. More than one control sample can be used. The presence of an amount of specific (selective) glycosphingolipid antibody binding in the test sample that is greater, by an amount that is statistically significant, than the amount of specific (selective) glycosphingolipid antibody binding in a comparable control sample, is indicative of a "positive" result which can be correlated with a diagnosis of the neuropathy. Alternatively, a "positive" result can also be considered a "positive" result for an initial screening assay; a positive initial screening assay indicates that further tests should be performed to detect the presence of the same or additional autoantibodies which contribute to, or are diagnostic for, the neuropathy.

Alternatively, the amount of antibody to a glycosphingolipid(s) of interest in the test sample can be compared with a "reference amount". A reference amount, as used herein, is an amount (e.g., a titer) of antibody to a glycosphingolipid of interest which has been previously determined to correlate with a particular disease state. For example, a reference amount can be determined by assessing the amount of antibody to glycosphingolipid(s) of interest in a set of samples from individuals having known diseases (e.g., neuropathies), as well as comparable control samples as described above, and determining what amount of antibody correlates with disease. An amount of antibody to a glycosphingolipid(s) of interest in the test sample that is equal to, or greater than, the reference amount, is indicative of a "positive" result which can be correlated with a diagnosis of the disease. Alternatively, as discussed above, a "positive" result can also be considered a "positive" result for an initial screening assay, indicating that further tests should be performed to detect the presence of the same or additional autoantibodies which contribute to, or are diagnostic for, the neuropathy.

The present invention also includes kits to be used in methods of the invention. Kits can include the following components: (1) a modified solid-phase reactant having carbonyl groups, and also having one or more glycosphingolipid(s) of interest attached thereto by amide bonds; and (2) labeled detector antibody that binds to the antibody to the glycosphingolipid(s) of interest. The detector antibody can be specific for the type of antibody (e.g., IgM, IgG or IgA) Detector antibody can comprise an antibody bound to a detectable agent, such as an enzyme, radioactive molecule, or fluorescent agent. If the detector antibody is bound to an enzyme that reacts with an added substrate to yield a colored product, such as horseradish peroxidase, the kit can also include the substrate.

The invention is now further illustrated by the following Exemplification.

EXEMPLIFICATION

COMPARISON OF ANTIBODY TITERS USING COVALENT-LINKAGE, ENZYME-LINKED IMMUNOSORBENT ASSAY (ELISA) PLATES

Linking of Antigen to Covalent Plates

Fresh, 1% EDAC in PBS (0.01 g EDC per ml PBS) was prepared, for 5.5 ml for each assay plate. An aliquot of SGPG stock was diluted into 1% EDAC to make the antigen coating solution at the desired concentration.

Each plate required 5.5 ml of coating antigen solutions. Plates were removed from foil pouches just prior to use, avoiding direct light that could damage the plates. Antigen coating solution (100 µl/well) was added to rows A, B, E, and F; rows C, D, G and H were left un-coated as the antigen blank wells. Coated plates were incubated in the dark at 4° C. overnight (16 hours). The coating solution was then aspirated, and the plates washed 3 times with 1% BSA. After the third wash, all plate wells were filled with 1% BSA, and the plates were blocked for at least 16 hours at 4° C. in the dark.

Sample Addition

A Tecan robot (Tecan USA, Durham, N.C.) was used to add diluted samples and controls to the plates. The plates were then incubated at 4° C. overnight in the dark.

Detection Antibody Probe and Colorimetric Reaction

Detection antibody (peroxidase conjugated goat anti-human IgM) was diluted in 1% BSA to the desired dilution, which was determined for each lot of antibody prior to use. Eleven ml of dilute detection antibody were used for each plate. Assay plates were aspirated and washed 6 times with 1% BSA, and then blotted dilute detection antibody solution (100 µl/well) was added to all assay plates, and the plates were incubated in the dark at room temperature for 2 hours. Substrate solution was then prepared: 100 mg of OPD and 12 µl of 30% hydrogen peroxide were added to 100 ml of 0.1 M citric acid (pH 4.5) to form substrate solution (11 ml per assay plate). All assay plates were then aspirated and washed 6 times with 1% BSA, and then blotted. Substrate solution (100 µl/well) was added to all assay plates, which were then covered to avoid light exposure. Pleases were incubated at room temperature, and read approximately 20 minutes after addition of substrate at 405 nm until both positive controls reached the established minimum OD validated for the positive control in use.

Results

Background noise

Results

A comparison of the background noise of the plate modified with carbonyl groups (Co-star DNA-Bind) and a plate modified with secondary amino groups (Nunc Covalink) was performed, as described above. A positive clinical SGPG control was used to represent the signal, and the background was a BSA buffer blank (absence of sample). Results are shown in Table 1 and The FIGURE.

TABLE 1

Comparison of Background Noise with Different ELISA Plates

| Plate | Signal | Background |
|---|---|---|
| Co-star DNA-Bind | 0.815 | 0.054 |
| Nunc Covalink | 0.815 | 0.354 |

The FIGURE demonstrates the results of the comparison of the signal to background noise of the plate having carbonyl groups attached thereon (the Co-star DNA-BIND plate) and the plate having secondary amino groups on its surface (NUNC Coating plate, Nunc; Roskilde, Denmark). It can be seen that the plate having carbonyl groups exhibited low background noise compared to the plate having secondary amino groups.

Reproducibility and Sensitivity

Experiments with SGPG linked to covalent plates demonstrated exceptional reproducibility. To measure day-to-day variability of the covalent plates, twenty-five SGPG clinical samples (serum in which antibodies to SGPG were present) were assayed on two separate days, as described above. The raw data average variation for the samples, measured by critical variance (C.V.) was equal to 7% (see Table 2). This value is well below the customary acceptable C.V. for clinical ELISA assays, which is 20% (see, e.g., Torbeck, L. D., *Assay Validation Basics*, Suffield Press, Skokie Ill., May 1996).

TABLE 2

Assay Variation

| Sample # | Day 1 raw data | Day 2 raw data | Average raw data | Std. Dev. raw data | % C.V. |
|---|---|---|---|---|---|
| 1 | 0.435 | 0.400 | 0.418 | 0.025 | 6% |
| 2 | 0.421 | 0.380 | 0.401 | 0.029 | 7% |
| 3 | 0.235 | 0.255 | 0.301 | 0.014 | 5% |
| 4 | 0.865 | 0.911 | 0.888 | 0.033 | 4% |
| 5 | 0.543 | 0.478 | 0.511 | 0.046 | 9% |
| 6 | 0.678 | 0.726 | 0.678 | 0.034 | 5% |
| 7 | 0.532 | 0.467 | 0.532 | 0.046 | 9% |
| 8 | 0.739 | 0.657 | 0.712 | 0.058 | 8% |
| 9 | 0.651 | 0.578 | 0.615 | 0.052 | 8% |
| 10 | 0.349 | 0.299 | 0.324 | 0.035 | 11% |
| 11 | 0.496 | 0.412 | 0.454 | 0.059 | 13% |
| 12 | 0.716 | 0.667 | 0.692 | 0.035 | 5% |
| 13 | 0.775 | 0.834 | 0.805 | 0.042 | 5% |
| 14 | 0.653 | 0.735 | 0.694 | 0.058 | 8% |
| 15 | 0.554 | 0.478 | 0.516 | 0.054 | 10% |
| 16 | 0.453 | 0.432 | 0.443 | 0.015 | 3% |
| 17 | 0.169 | 0.203 | 0.186 | 0.024 | 13% |
| 18 | 0.178 | 0.156 | 0.167 | 0.016 | 9% |
| 19 | 0.564 | 0.556 | 0.560 | 0.006 | 1% |
| 20 | 0.435 | 0.378 | 0.407 | 0.040 | 10% |
| 21 | 0.902 | 0.923 | 0.913 | 0.015 | 2% |
| 22 | 0.334 | 0.299 | 0.317 | 0.025 | 8% |
| 23 | 0.567 | 0.533 | 0.550 | 0.024 | 4% |
| 24 | 0.456 | 0.467 | 0.462 | 0.008 | 2% |
| 25 | 0.786 | 0.734 | 0.760 | 0.037 | 5% |
| | | | | Average % C.V. | 7% |

% C.V. = (Std. Dev.) ÷ (Average) × 100

An ELISA for SGPG can be used as a preliminary screening test for another clinical assay, such as the MAG Western, in identifying the etiology of neurological symptoms. The MAG Western is used to detect antibodies to myelin associated glycoprotein; anti-MAG antibodies are associated with peripheral neuropathies (see, e.g., demyelinating sensory or sensorimotor neuropathy associated with MAG antibodies described in Quarles, R. H. and Weiss, M. D., *Muscle Nerve* 22(7):800–22 (1999)). The ELISA for SGPG is a preliminary screening assay; samples testing positive in the SGPG assay are then tested in the MAG Western assay. A positive result in the SGPG assay, followed by a negative result in the MAG Western assay, is considered a false positive. However, a positive result in the SGPG assay, followed by a positive result in the MAG Western assay, suggests an autoimmune etiology for neurological symptoms (and thus can be diagnostic for the neuropathy).

A series of clinical samples from individuals previously tested with the MAG Western were tested as described above, using both a traditional plate (Falcon polystyrene plate) and a plate modified with carbonyl groups allowing amide linkage of glycosphingolipids to the plates (Co-star DNA-BIND plate). The results indicated that the MAG negative samples (sample which had no binding of antibodies in the MAG Western assay) showed identical negative SGPG values with both plates. Surprisingly, however, 90% (27 of 30) of the MAG positive samples (samples which showed binding of antibodies in the MAG Western assay) had higher antibody titers on the modified plates than on traditional plates. Results are shown in Table 3.

TABLE 3

Comparison of SGPG Antibody Titers for MAG Western positive samples (higher titer values are boldfaced)

| Sample # | Traditional Plate SGPG Titer | Covalent Plate SGPG Titer |
|---|---|---|
| 1 | 6400 | 409600 |
| 2 | 51200 | 819200 |
| 3 | 102400 | 819200 |
| 4 | 204800 | 204800 |
| 5 | 25600 | 409600 |
| 6 | 51200 | 204800 |
| 7 | 102400 | >819200 |
| 8 | 819200 | >819200 |
| 9 | 12800 | 102400 |
| 10 | 409600 | >819200 |
| 11 | 102400 | >819200 |
| 12 | 204800 | >819200 |
| 13 | 819200 | >819200 |
| 14 | 102400 | 819200 |
| 15 | 12800 | 204800 |
| 16 | 819200 | >819200 |
| 17 | 819200 | 204800 |
| 18 | 51200 | 204800 |
| 19 | 1600 | 6400 |
| 20 | 25600 | 819200 |
| 21 | 51200 | 204800 |
| 22 | 409600 | 204800 |
| 23 | 409600 | >819200 |
| 24 | 25600 | 204800 |
| 25 | 819200 | >819200 |
| 26 | 51200 | 409600 |
| 27 | 3200 | 102400 |
| 28 | 25600 | 204800 |
| 29 | 3200 | 204800 |
| 30 | 102400 | 819200 |

These results demonstrate that the assay using a plate modified with carbonyl groups allowing amide linkage of glycosphingolipids to the plates is significantly more sensitive for antibodies in the MAG Western positive samples. Thus, it serves as a more sensitive screening test for samples which should be tested using the MAG Western assay.

While this invention has been particularly shown and described with references to preferred embodiments thereof, it will be understood by those skilled in the art that various changes in form and details may be made therein without departing from the scope of the invention encompassed by the appended claims. The teachings of all references cited herein are incorporated by reference in their entirety.

What is claimed is:

1. A method of determining in a test sample the amount of antibody to at least one glycosphingolipid of interest, comprising the steps of:

a) providing a glycosphingolipid modified solid-phase reactant, the glycosphingolipid modified solid-phase reactant comprising a modified solid-phase reactant having carbonyl groups attached thereon and the glycosphingolipid of interest linked to the modified solid-phase reactant by an amide bond between an amino group of the glycosphingolipid of interest and a carbonyl group attached to the modified solid-phase reactant;

b) contacting the glycosphingolipid modified solid-phase reactant with a test sample, thereby forming a contacted glycosphingolipid modified solid-phase reactant;

c) maintaining the contacted glycosphingolipid modified solid-phase reactant under conditions to allow antibody to the glycosphingolipid of interest, if present in the sample, to bind to the glycosphingolipid of interest linked to the modified solid-phase reactant; and d) determining the amount of antibody to the glycosphingolipid of interest that is bound to the glycosphingolipid of interest linked to the modified solid-phase reactant.

2. The method of claim 1, wherein the glycosphingolipid of interest is sulfoglucuronyl paragloboside.

3. The method of claim 1, wherein the modified solid-phase reactant additionally comprises at least one control antigen attached to the modified solid-phase reactant.

4. The method of claim 3, wherein the control antigen is selected from the group consisting of: a glycolipid, a glycoprotein, and a carbohydrate.

5. The method of claim 1, wherein the solid-phase reactant is a microtiter plate.

6. The method of claim 1, wherein the amount of antibody to the glycosphingolipid of interest that is bound to the glycosphingolipid of interest attached to the modified solid-phase reactant is determined by incubating the contacted glycosphingolipid modified solid-phase reactant with a developing reagent.

7. The method of claim 6, wherein the developing reagent comprises a detection antibody that binds to antibody to the glycosphingolipid of interest.

8. The method of claim 7, wherein the detection antibody is conjugated to an enzyme.

9. The method of claim 7, wherein the detection antibody is conjugated to a fluorophore.

10. The method of claim 7, wherein the detection antibody is iodinated.

* * * * *